United States Patent [19]

Denis

[11] Patent Number: 4,603,024
[45] Date of Patent: Jul. 29, 1986

[54] METHOD OF MAKING A CORRECTING AND/OR ASSISTING SOLE BY MOLDING

[75] Inventor: Marc Denis, Gaillon, France
[73] Assignee: Sipse, Gaillon, France
[21] Appl. No.: 706,484
[22] Filed: Feb. 28, 1985

[30] Foreign Application Priority Data

Mar. 1, 1984 [FR] France ............... 84 03221

[51] Int. Cl.$^4$ ............................... B29C 33/40
[52] U.S. Cl. ................... 264/223; 156/212; 264/154; 264/226; 264/227; 425/2
[58] Field of Search ............ 264/40.5, 220, 221, 264/222, 223, 224, 226, 227, 154; 156/212; 425/2

[56] References Cited

U.S. PATENT DOCUMENTS

| | | | |
|---|---|---|---|
| 1,914,049 | 6/1933 | Smith | 264/223 |
| 2,547,419 | 4/1951 | Sugarman et al. | 264/223 X |
| 2,894,288 | 7/1959 | Brindis | 264/223 |
| 3,398,221 | 8/1968 | Sherman et al. | 264/223 |
| 3,995,002 | 11/1976 | Brown | 264/223 |
| 4,454,090 | 6/1984 | Saumell | 264/222 |

FOREIGN PATENT DOCUMENTS

2471181 12/1980 France .

Primary Examiner—Jan Silbaugh
Assistant Examiner—Harold Pyon
Attorney, Agent, or Firm—Fiddler & Levine

[57] ABSTRACT

A print is made of the sole of a foot in a block (1) of modelling clay. If necessary the print is corrected for orthopedic reasons. A rigid shape (23) is cast in the print, and after unmolding, the contour (26) of a sole to be made is marked on the shape in relief. The shape is then used to mark said contour in hollow form in the footprint. The block is then cut through along said contour and the central portion of the block is removed. The rigid shape is reinserted in the remaining peripheral portion of the footprint, and a sole is cast inside the peripheral portion and on the rigid shape. A first sole may be made in a single session in the presence of the patient. Thereafter, the rigid shape may be conserved, and used to make any subsequent soles that may be necessary without requiring the patient to be present.

11 Claims, 8 Drawing Figures

U.S. Patent    Jul. 29, 1986    4,603,024
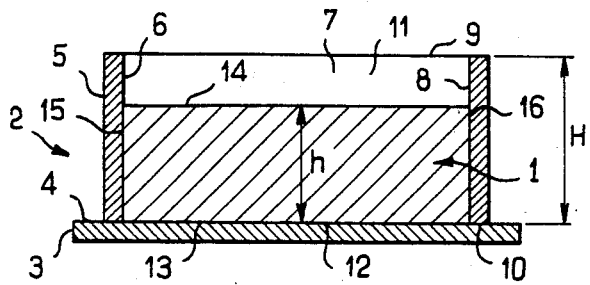
FIG.1
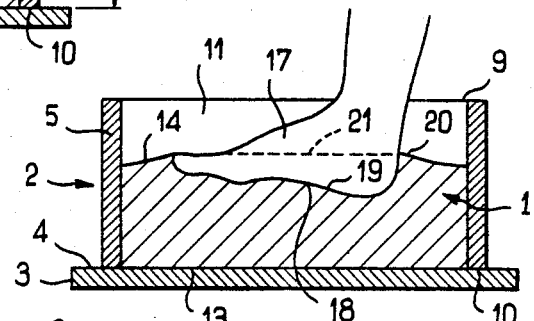
FIG.2
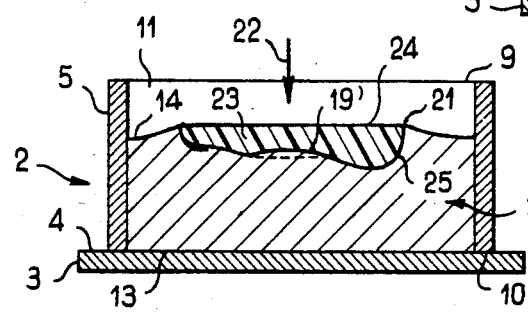
FIG.3
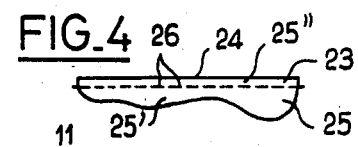
FIG.4
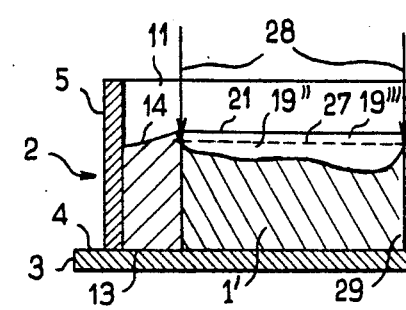
FIG.5
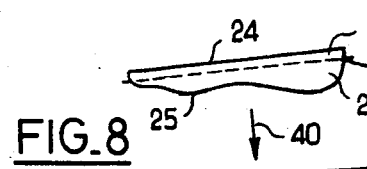
FIG.6
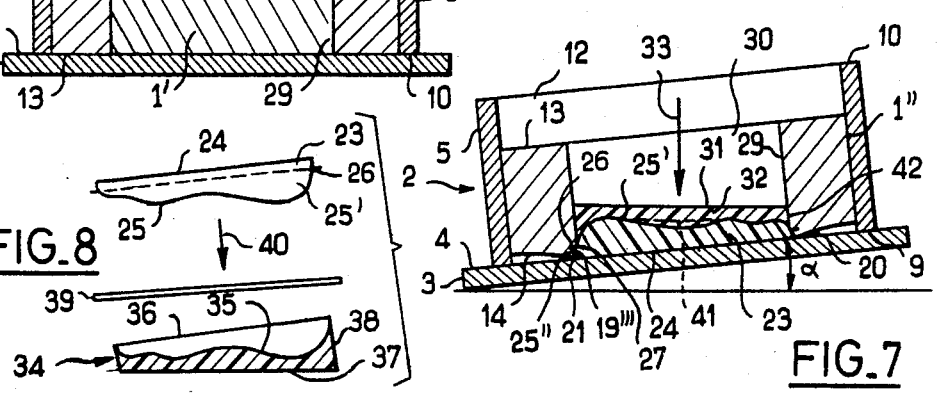
FIG.8
FIG.7

METHOD OF MAKING A CORRECTING AND/OR ASSISTING SOLE BY MOLDING

The present invention relates making a correcting and/or assisting sole by molding for a foot which may or may not be painful.

The term "assisting" sole is used to designate a sole which is a close fit to the natural shape of a foot, while the term "correcting" sole is used for a sole having a different shape from the natural shape of the foot, said different shape being determined by a doctor.

BACKGROUND OF THE INVENTION

In one known method, for example as described in the introduction of French published certificate of utility number 2 471 181, a correcting and/or assisting sole is made by the following sequence of steps:

(a) taking a print of the sole of the foot in an approximately plane face of block of modelling clay;
(b) casting a rigid shape in said footprint;
(c) unmolding said shape; and then bending over the shape a sheet of material, such as leather, suitable for plastically deforming and subsequently retaining the desired curvature, e.g. by applying a synthetic resin which is subsequently hardened or by gluing to a plate of cork having a correspondingly shaped hollow formed therein, then optionally adding corrective bumps to the sheet, and finally covering it with a leather insole.

This known method requires numerous operations, and is thus lengthy and expensive; further it suffers from requiring action both by an orthopedic doctor who is generally not capable of manufacturing the entire sole, but who is needed to specify the location and shape of any bumps that need adding, and by a prosthesis technician to build the sole in a workshop as a function of the doctor's prescription. Such two-stage action increases the time taken between the sole being prescribed, the patient trying it on, any necessary corrections being made to the added bumps, and final delivery of the sole.

To remedy these drawbacks, the above-mentioned certificate of utility proposes making an orthopedic sole by direct molding to the foot of the patient using a material which is suitable initially for deforming plastically to take up the required shape, and which is subsequently capable of solidifying rapidly.

This method does indeed have the advantage of being quick, firstly because the sole is made by direct molding, and secondly because the molding may be performed in the doctor's consulting room. However, it requires the patient to be present not only when a first sole is made for the patient, but also on every subsequent occasion on which the sole needs to be replaced.

Preferred implementations of the present invention remedy these drawbacks by proposing a method of making a correcting and/or assisting sole by molding in a manner which may be performed by the orthopedic doctor, i.e. by a method which does not require a great deal of time or equipment, and which also leaves the doctor or the technician with a rigid shape capable of being reused to renew the sole without requiring the patient to be present each time. In addition, the invention can be used to achieve these ends relatively cheaply.

SUMMARY OF THE INVENTION

To this end the present invention provides a method of making a correcting and/or assisting sole by molding, the method repeating steps (a) to (c) above, with step (c) further including retaining the foot print, the method then comprising the following steps:

(d) marking the shape in relief with the contour of the sole to be made;
(e) reinserting the shape into the print to mark said contour as a hollow in said print, said mark separating a central portion of the print from a peripheral portion thereof;
(f) removing the shape from the marked print and retaining both the shape and the marked print;
(g) cutting the block through along the said marking hollow approximately perpendicularly to the said face to detach a central portion of the block bearing the central portion of the print from a peripheral portion thereof bearing the peripheral portion of the print;
(h) separating the central portion of the block from the peripheral portion of the block and retaining the peripheral portion of the print;
(i) placing the peripheral portion of the block on a support via the said face and reinserting the shape in the peripheral portion of the print;
(j) molding a sole on the shape inside the peripheral portion of the block; and
(k) unmolding the sole.

If a correcting sole is to be made, the print is modified between steps (a) and (b) as a function of the orthopedic prescription.

It may be observed that in step (d) a rigid shape is obtained which may be subsequently used to make a new print complete with contour mark in an approximately plane face of a block of modelling clay, thus enabling steps (f) onwards to be subsequently performed without taking a new print of the patient's foot.

Thus once a first sole has been made, further identical soles can be made without the patient being present.

The rigid shape and the sole may be molded from quick-setting synthetic resins which are well known in the plastics materials industry, and no complicated equipment is required even to make the first sole. Indeed it may readily be made in an orthopedic doctor's consulting room while the patient is present. The patient can thus begin by the initial print-taking step (a) and end by trying on the resulting sole all on a single occasion. Thus, if need be, feed-back from the patient may be used immediately to restart the method with different modifications being made to the print between steps (a) and (d) if the initial modifications turn out to be unsatisfactory.

The method of the present invention is cheap to implement, not only because cheap raw materials are used, but also becuase it is very quick and may be performed by a single person in ordinary consulting room premises.

BRIEF DESCRIPTION OF THE DRAWINGS

An implementation of the invention is described by way of example with reference to the accompanying drawing which constitutes an integral part of the description. In the drawing:

FIGS. 1 to 3 are sections on the same vertical plane showing steps (a) and (b) of the method;

FIG. 4 shows the rigid shape with a mark in relief delimiting the shape of the sole to be made, as obtained at step (d);

FIGS. 5 to 7 are sections on the same plane as FIGS. 1 to 3 showing steps (e) onwards of the method; and FIG. 8 is a similar section through the resulting sole and showing one way in which it may be finished.

MORE DETAILED DESCRIPTION

Reference is made initially to FIG. 1 where 1 designates a block of modelling clay. The block is generally rectangular in shape and is removably received in a rigid box 2 defined by a base plate 3 having a top face 4, and by a surrounding wall 5 which simply rests via a bottom edge 10 on the top face 4 of the base plate. The surrounding wall 5 has four inside plane faces, only three of which referenced 6, 7 and 8 are visible in the figures. These faces are adjacent to one another in pairs and also to the top face 4 of the base plate 3. They are also perpendicular to one another in pairs and to the base plate 3. The surrounding wall 5 is open top and bottom (11 and 12) having the above-mentioned bottom edge 10 and a similar top edge 9 which is plane and parallel to the bottom edge 10.

As can be seen in FIG. 1, prior to the method being implemented, the block 1 has a plane bottom face 13 in flat contact with the top face 4 of the base plate 3 inside the surrounding wall 5. The plane bottom face 13 of the block 1 is thus coplanar with the said bottom edge 10 of the surrounding wall. The block further has a top face 14 which is also plane and which is disposed below the top edge 9 of the surrounding wall 5. The height h of the top face 14 above the base plate 3 is thus less than the height H of the top edge 9 above the same base plate. The block 1 is in contact with the inside faces such as 6 to 8 of the surrounding wall 5, but does not stick thereto so as to be free to slide inside the surrounding wall. In other words, the block 1 has a face 15 which is in contact with and free to slide over the face 6 of the surrounding wall, a face 16 in contact with the face 8, etc., with the side faces of the block being plane and perpendicular to one another in pairs and also perpendicular to the top and bottom faces 13 and 14.

The first and most highly skilled step of the invention consists in using the assembled box 2 and block 1 to obtain a suitable print of the patient's foot. The foot 17 is inserted into the box 2 through the open top face 11 thereof and the sole of the foot 18 for which a matching footwear sole is to be made is firmly applied against the top face 14 of the block 1, thus making a negative print 19 thereof in the modelling clay. If necessary, and as illustrated in FIG. 2, insufficient penetration of the foot 17 into the block 1 is corrected by raising a rim 20 of modelling clay around the foot 17, taking clay from the areas of the top face 14 which are immediately adjacent to the surrounding wall 5. It is best to keep to the natural shape of the foot and its natural orientation relative to the leg while the foot is being pressed into the clay. In particular, care should be taken to see that the toes are neither splayed nor raised and that the leg is vertical relative to the supposedly horizontal top face 14 of the block. In addition, by pressing more particularly on the outside of the foot it is possible to obtain a degree of automatic correction directly due to the print itself for defects in ankle positioning, or in other words for flat or offset arches. Preferably, the rim 20 around the foot 17 is shaped so that its top edge 21 is as plane as possible and is as parallel as possible with the face 13 of the block 1.

The foot 17 is then removed from the print 19 obtained in this manner, which print is upwardly delimited by the rim 20, and in particular by the top edge 21 thereof.

Then, without modifying the print 19 if an assisting sole is required, or after modifying the print 19 as a function of an orthopedic prescription if a correcting sole is required (as illustrated by a bump 19' in FIG. 3), synthetic resin or "plastic" in the liquid or pasty state is cast into the print 19 as indicated by arrow 22 in FIG. 3. The print 19 or the modified print 19' is filled with said plastic up to the top edge 21 of the 20, which edge is kept horizontal. Then, depending on the nature of the plastic cast into the print 19, either the plastic is left to set, or else it is subjected to a treatment to make it set in the print 19. In either case, a positive shape 23 is obtained having a plane top surface 24 which is defined by the level to which the print 19 was filled, i.e. is coplanar with the edge 21, and a downwardly directed face 25 which meets the plane face 24 all round its perimeter and which exactly reproduces the print 19 or the modified print 19' but as a positive shape.

A quick-setting plastic material is preferred for making the shape 23, but other plastic materials could also be used, as could any other material which is easy to cast and which then sets.

For example, good results have been obtained by making the shape 23 from a two-component polyurethane resin which is impregnated:

either with hydrated alumina, e.g. 60% by weight alumina and 40% by weight resin in order to make the resulting shape 23 easier to work;

or else with solid or hollow microspheres of glass, e.g. 35% by weight microspheres to 65% by weight resin for the same reason and to lighten the shape.

In any case, the material selected for the shape 23 must be perfectly rigid once it has set.

Once the material constituting the shape 23 has set in the print 19 or the modified print 19', the shape 23 is unmolded while taking care to preserve the print, and then as shown in FIG. 4, the contour 26 of the sole to be made is marked in relief on the curved face 25 of the shape.

This marking may be done in several different ways, for example by inserting nails or staples into the shape. The contour may be marked as a continuous line or as a line with discontinuities, the important thing is for the contour to be completely determined by the relief on the shape.

The shape 23 is then put back in the print 19 or modified print 19' so that the contour 26 marked in relief around the shape 23 is transferred in the form of a hollow mark 27 in the block 1 around the print. This step is shown in FIG. 5. This hollow mark 27 delimits a central portion 19'' and a peripheral portion 19''' in the print 19 or the modified print 19'.

The shape 23 is then removed together with its relief marking 26 from the print and its hollow marking 27. Both the shape and the print are preserved. As indicated at 28 in FIG. 6, the block 1 is then cut through following the hollow-marked contour 27 and approximately perpendicularly to the top face 14 (and thus also to the bottom face 13), thereby detaching a central portion 1' of the block bearing the central portion 19'' of the print from a peripheral portion 1'' of the block bearing the peripheral portion 19''' of the print. Clearly the term "print" denotes either the natural print 19 or the modified print 19' as the case may be.

It may be observed that during all the steps described so far, the box 2 and the block 1 have remained in the same position with the faces 4 and 14 and the edge 9 remaining approximately horizontal and facing upwardly.

In the following step the central portion 1' of the block is separated from the peripheral portion 1" and at least the peripheral portion is preserved together with the peripheral portion 19''' of the print 19 or the modified print 19'.

Then, as shown in FIG. 7, the shape 23 is reinserted in the peripheral portion 19''' of the print 19 or the modified print 19' so that the contour 26 in relief coincides with the hollow contour 27, and the assembly constituted by the surrounding wall 5, the peripheral portion 1" of the block and the reinserted shape 23 is turned upsidedown so that the top edge 9 of the surrounding wall 5 comes into contact with the top face 4 of the base plate 3. Given the difference between the height of the wall H and the thickness h of the block 1, the peripheral portion 1" of the block then slides relative to the wall 5 so that the top 21 of the rim 20 comes into contact with the top face 4 of the base plate 3, thus causing the plane face 24 of the shape 23 also to come into contact therewith.

As can be seen in FIG. 7, the inside wall 29 of the peripheral portion 1" as cut through at 28 delimits a cavity 30 which has an open top face accessible via the now uppermost opening 12 of the surrounding wall 5. The bottom of the cavity 30 is closed by the shape 23, or more precisely by the central portion 25' of its curved face 25 up to the contour in relief 26 which is engaged in the hollow 27, and which coincides with the inside wall 29. This visible central portion 25' of the shape 23 at the bottom of the cavity 30 corresponds to the central portion 19" of the print 19 and includes the modifications made thereto, if any. The surrounding portion 25" of the shape 23 between the contour 26 and the plane face 24 is a close fit in the peripheral portion 19''' of the print (see also FIG. 4).

It is thus possible to insert any desired substance into the cavity 30 via the upwardly directed opening 12 of the wall 5. The first substance to be inserted is a layer of sealing material for closing any gaps or leaks at the join between the shape 23 and the peripheral portion 1" where the contour lines 26 and 27 meet. Advantageously, the material used is also suitable for facilitating subsequent unmolding of a sole cast in the cavity 30 and is therefore spread over the entire surface of the cavity 30 which is likely to come into contact with sole-constituting material. A suitable sealing and unmolding material is Codex vaseline, but other materials could also be used without going beyond the scope of the invention.

The sole is then molded in the cavity 30 by casting a liquid or pasty material therein which is subsequently allowed or caused to set. The material used is generally chosen as a function of the desired hardness or softness of the resulting sole.

Non-exclusive examples of suitable materials for making the sole include: a polyurethane elastomer either with or without powdered natural rubber impregnated therein; a silicone elastomer, or a rubber elastomer. The person skilled in the art can readily formulate such materials to obtain soles of the desired consistency.

Other materials may naturally be used without going beyond the scope of the invention.

Prior to casting, the cavity 30 may be partitioned so as to delimit predetermined zones on the central portion 25' of the curved face 25 of the shape 23. Different materials may then be cast into different zones, thus enabling the characteristics of the sole to be varied. It is also possible to cast successive layers of different materials. In this case, the first layer is the layer which fills the hollows in the central portion of the curved face 25, e.g. the portion corresponding to the arch of the foot. Thus, by casting initially with a material which sets relatively hard, and then casting with a material which sets relatively soft, it is possible to arrange for the portion of the sole which corresponds to the arch of the foot to be stiffer than the rest of the sole.

The casting and setting operations in the cavity 30 are advantageously performed after tilting the assembly comprising the shape 23, the peripheral portion 1" of the block, and the box (i.e. the base plate 3 and the upsidedown surrounding wall 5 thereon) so that the coplanar faces 4 and 24 and the edge 21 are at a predetermined angle $\alpha$ to the horizontal. The angle $\alpha$ is chosen to obtain a top horizontal surface 31 on the material 32 cast in the cavity 30 which is at a desired angle to the central portion 25' of the curved face 25 of the shape 23. If a plurality of different layers are cast, it is quite possible to use a different angle $\alpha$ for each layer. The angle $\alpha$ is determined as a function of the orthopedic prescription. When the last (or only) layer is cast and the foot is normal with respect to the positions of its four main load-carrying regions, the angle $\alpha$ is chosen in such a manner that the images in the curved face 25 of said regions lie substantially in the plane of the top horizontal surface 31, thereby enabling the end of casting to be determined as the moment when all of said images are just covered by the material of the last (or only) layer. This gives rise to a sole which is as thin as possible and thus as light as possible. When the foot is not normal in this respect, the end of casting is still generally determined as a function of the positions of the said images, but in a manner prescribed by the doctor.

Further, as a function of the prescription, it is possible to embed one or more prefabricated components in the sole while any part thereof is being cast. Such components may be specially shaped stiffeners 41, for example.

After each casting operation, the casting material is either allowed to set or else it is caused to set, depending on the nature of the material used. If several layers are cast, each layer is set prior to casting the next layer.

The desired sole 34 is thus obtained inside the cavity 30 and is then unmolded. In other words, the shape 23 is disengaged from the peripheral portion 1" of the block. the various component parts shown in FIG. 7 are generally separated from one another and the shape 23 together with its contour 26 in relief is retained for possible future use, as follows:

a new print is made as described with reference to FIG. 2, but from the shape 23 rather than from the patient's foot, the new print is made in the approximately horizontal surface 14 of a block 1 of modelling clay as before, and the raised contour of the sole is naturally marked in the new print;

the block 1 is cut through approximately perpendicularly to the face 14 as described with reference to FIG. 6;

the central portion of the block is separated from the peripheral portion, and the peripheral portion is retained together with the peripheral portion thereon of the print;

the shape is reinstalled in the peripheral portion of the block and the assembly is turned upsidedown as before;

a new sole is cast on the shape 23 inside the peripheral portion of the block by any of the techniques described with reference to FIG. 7; and the resulting sole is unmolded.

Thus, by archiving the shape 23 together with its raised marking 26, an orthopedist can readily supply patients with new soles without requiring the patient to make a new foot print each time, and without having to repeat the corrections to the print each time.

As for the modelling clay, it can be kneaded back into a single uniform block and reused for another patient.

After being unmolded, the sole 34 has a hollow face 35 which is a negative reproduction of the central portion 25' of the curved face 25 of the shape 23 and which is delimited by a plane edge 36 which is the image of the marked contour 26 and 27. The sole further has a plane base face 37 corresponding to the top face 31 of the last (or only) layer 32, and a side face 38 which connects the face 37 to the edge 36. The side face 38 is formed by the zone of contact 42 between the inside wall 29 of the peripheral portion 1" and the casting material. Various finishing operations may be applied to the sole.

The hollow face 35 may be finished by covering it with a leather insole 39. The insole is glued to the face 35 and is advantageously pressed down against it by the shape 23, as indicated at 40 in FIG. 8. the other faces 37 and 38 may need paring down to be fitted inside a shoe.

The present invention relates not only to the method of making a sole as described above, but also to a sole made by the method and to a shape together with its contour in relief as used in the method.

It will be understood that the invention is capable of numerous variants without going beyond the scope of the claims. For example, the modelling clay may be of such a consistency that the surrounding wall 5 may be omitted thereby reducing the box 2 to a simple base plate 3.

Finally, the high accuracy and the great simplicity of the method of the present invention should be noted. They are due, in particular, to the use of a block of modelling clay bearing a print which is used both as a mold for obtaining a rigid positive capable of being archived for reuse, and also as a mold for making a flexible negative, ie. the sole itself.

I claim:

1. A method of making a correcting and/or assisting sole by molding, the method comprising the following succession of steps:
   (a) taking a print of the sole of a foot in an approximately plane face of a block of modelling clay;
   (b) casting a rigid shape in said footprint;
   (c) unmolding said shape;
   (d) marking the shape in relief with the contour of the sole to be made;
   (e) reinserting the shape into the print to mark said contour as a hollow in said print, said mark separating a central portion of the print from a peripheral portion thereof;
   (f) removing the shape from the marked print and retaining both the shape and the marked print;
   (g) cutting the block through along the said marking hollow approximately perpendicularly to the said face to detach a central portion of the block bearing the central portion of the print from a peripheral portion thereof bearing the peripheral portion of the print;
   (h) separating the central portion of the block from the peripheral portion of the block and retaining the peripheral portion of the print;
   (i) placing the peripheral portion of the block on a support via the said face and reinserting the shape in the peripheral portion of the print;
   (j) molding a sole on the shape inside the peripheral portion of the block; and
   (k) unmolding the sole.

2. A method according to claim 1, wherein at step (k) the shape together with its contour in relief is removed from the peripheral portion of the block and is preserved for subsequent reuse in a method which consists in taking a print of the shape together with a hollow mark of its contour in an approximately plane face of a block of modelling clay, and then repeating steps (f) through (k).

3. A method according to claim 1, wherein the print of the foot is modified between steps (a) and (b) as a function of an orthopedic prescription.

4. A method according to claim 1, wherein the rigid shape is molded at step (b) by casting settable material in a liquid or pasty state into the print of the foot, and then causing or allowing said material to set while in the print.

5. A method according to claim 1, wherein the sole is molded at step (j) by casting at least one layer of settable material in a liquid or pasty state into the peripheral portion of the block and onto the shape, and then causing or allowing said material to set inside said peripheral portion on said shape.

6. A method according to claim 5, wherein zones of the shape within the peripheral portion of the block are partitioned off during step (j) prior to casting, and wherein different settable materials are cast on different zones of the shape.

7. A method according to claim 5, including an additional step between steps (i) and (j), said additional step consisting in sealing the shape to the peripheral portion of the block.

8. A method according to claim 5, wherein step (j) is performed with the support tilted at an angle which is predetermined as a function of an orthopedic prescription.

9. A method according to claim 5, wherein at least one prefabricated component is embedded in the sole during casting thereof.

10. A method according to claim 1, including an additional step between steps (i) and (j), said additional step consisting in covering the shape and the peripheral portion of the block in a material suitable for facilitating unmolding.

11. A method according to claim 1, wherein the shape is preserved at step (k) and wherein it is subsequently used to press down a sheet of lining material against the sole.

* * * * *